United States Patent [19]

Parham et al.

[11] 4,454,347
[45] Jun. 12, 1984

[54] PROCESS FOR PURIFICATION AND ISOLATION OF DIAMINOPHENYLINDANE

[75] Inventors: Marc E. Parham, Sharon, Mass.; Stephen A. Spearman, West Warwick, R.I.; Gleason O. Cookson, Taunton, Mass.

[73] Assignee: Ciba-Geigy Corporation, Ardsley, N.Y.

[21] Appl. No.: 465,744

[22] Filed: Feb. 11, 1983

[51] Int. Cl.$^3$ .............................................. C07C 85/26
[52] U.S. Cl. ..................................... 564/428; 564/437
[58] Field of Search ................................ 564/428, 437

[56] References Cited

U.S. PATENT DOCUMENTS 2,048,781  7/1936  Craig ............................. 564/428 X
4,096,123  6/1978  Molloy .......................... 564/428 X Primary Examiner—Paul F. Shaver
Attorney, Agent, or Firm—Luther A. R. Hall

[57] ABSTRACT

Crystalline 5(6)-amino-1-(4-aminophenyl)-1,3,3-trimethylindane is made by crystallizing the diamino reaction mass from a toluene/heptane solution. The material has been previously purified through a combination of acetic acid washing and treatment with acidic clay. The diamino material, also known as DAPI, is a potential stabilizer, curing agent, and one of the monomers used to produce a polyimide resin.

3 Claims, No Drawings

PROCESS FOR PURIFICATION AND ISOLATION OF DIAMINOPHENYLINDANE

FIELD OF THE INVENTION

This invention pertains to a method of preparing 5(6)-amino-1-(4-aminophenyl)-1,3,3-trimethylindane, a monomer for XU 218 polyimide in a purified, crystalline form.

BACKGROUND OF THE INVENTION

Polyimides are known for their thermal-oxidative stability and XU 218, which is copolymer of benzophenonetetracarboxylic dianhydride (BTDA) and 5(6)-amino-1-(4-aminophenyl)-1,3,3-trimethylindane (DAPI) is one such polyimide available from CIBA-GEIGY Corporation. The composition of the copolymer is described in U.S. Pat. No. 3,856,752. Use of DAPI as an epoxy curing agent is described in U.S. Pat. No. 3,983,092.

Critical to the production of acceptable quality XU 218 is the purity of the two monomers, BTDA and DAPI, and the stoichiometric ratio of these two compounds. Prior to this invention, crystallization and purification of the DAPI monomer was not carried out, and without adequate purity, the XU 218 polyimide could not be reproducibly made. The DAPI was previously used as a melt in toluene which leads to severe handling problems, oxidation, potential health hazards and economic disadvantages due to off-standard polymer production. The full economic potential of the DAPI monomer can be realized through the crystallization and purification of the compound.

The preparation of these diamines is described in an article by J. C. Petropoulos et al., J. Amer. Chem. Soc., 80 1938 (1957), in U.S. Pat. Nos. 2,855,420 and particularly 3,983,092.

The diamines are obtained as a mixture of isomers as is described in U.S. Pat. No. 3,983,092 as a low melting glassy solid which may contain sufficient impurities to interfere at times with the subsequent polymerization step to form the polyimide.

A more highly purified diamine such as would be obtained in a crystallized form would be expected to yield the desired polyimide in a reproducible fashion.

OBJECTS OF THE INVENTION

The object of this invention is to provide a method or preparing 5(6)-amino-1-(4-aminophenyl)-1,3,3-trimethylindane in a crystalline form.

A further object of the invention is a process to purify the crude diamino material through the elimination of higher molecular weight oligomers of the DAPI which adversely affect the properties of the polyimide resin. In this manner, crude 5(6)-amino-1-(4-aminophenyl)-1,3,3-trimethylindane can be converted to a usable form.

DETAILED DISCLOSURE

The invention pertains to a process of preparing 5(6)-amino-1-(4-aminophenyl)-1,3,3-trimethylindane in a crystalline form, with the material having sufficient purity for subsequent polymerization.

The instant invention relates more specifically to a process for preparing 5(6)-amino-1-(4-aminophenyl)-1,3,3-trimethylindane in a purified, crystalline form which comprises (a) mixing a solution of toluene or xylene and 5(6)-amino-1-(4-aminophenyl)-1,3,3-trimethylindane with an aqueous solution of a lower alkane monocarboxylic acid at room temperature to extract polyamino impurities, (b) treating the toluene or xylene layer from step (a) with an acidic clay at room temperature to complete the removal of polyamino impurities by absorption thereon, (c) concentrating the toluene or xylene layer from step (b) to about a 50% by weight solution of 5(6)-amino-1-(4-aminophenyl)-1,3,3-trimethylindane by heating to a temperature between 60° and 80° C. under a pressure of 100 to 200 mm Hg to remove excess toluene or xylene, (d) slowly cooling the solution from step (c) with continual agitation first to room temperature, then, following an extended hold of 8 to 15 hours at room temperature, with continued slow cooling to a temperature between 0° and 5° C. to initiate crystallization of the product, and finally (e) charging at 0° to 5° C. to the crystallizing mass from step (d) an alkane of 5 to 8 carbon atoms or a mixture of such alkanes in a weight equal to that of the toluene or xylene present to facilitate crystallization of the desired product which is then isolated.

Still more specifically the process of this invention involves mixing a toluene solution of 5(6)-amino-1-(4-aminophenyl)-1,3,3-trimethylindane with aqueous acetic acid at a temperature of 20°–25° C. and, after splitting off the aqueous acetic acid phase, treating the toluene solution with an acidic clay at a temperature of 20°–25° C. After the clay is filtered from the toluene solution, then the DAPI/toluene solution is rinsed with deionized water to reduce the ionic content. Toluene is then distilled, preferably between 65° and 70° C., under a pressure of 100 to 200 mm Hg, with agitation to achieve a DAPI composition of 50% by weight, and then slowly cooling the DAPI/toluene solution, with continued agitation, to a temperature between 23° and 25° C. After holding the solution at this temperature for an extended time, the solution is then slowly cooled, with continued agitation, to a temperature between 0° and 5° C. n-Heptane is then slowly added to the crystallization mass at a temperature between 0° and 5° C. and after holding for one hour, the DAPI product is isolated.

The instant process may be applied to any form of 5(6)-amino-1-(4-aminophenyl)-1,3,3-trimethylindane, either crude crystalline DAPI, toluene/DAPI melt, or DAPI wet. The instant process affords a way of converting off-standard DAPI containing polyamino impurities, into high quality crystalline material (>99% DAPI).

Low levels of water or other polar solvents can facilitate the purification of DAPI with the acidic clay. It is expedient to add a small amount (between 0 and 2.5%) of methanol during the acidic clay treatment to improve the adsorption of the polyamino materials.

Toluene or xylene may be used as the aromatic hydrocarbon solvent to dissolve the 5(6)-amino-1-(4-aminophenyl)-1,3,3-trimethylindane. Preferably toluene is used.

While an aqueous solution of any lower alkane monocarboxylic acid, such as formic, acetic or propionic acid, may be used to extract the polyamino impurities in step (a), acetic acid is preferred for matters of availability and economics.

Any of a variety of commercially available acidic clays may be used to absorb the residual polyamino impurities in step (b). Such acidic clays are available under the trademark Filtrol and Filtrol grade 1, 4 or 13 was found to be particularly preferred.

In step (c) the concentration of the toluene or xylene solution of the instant diamine to a 50% by weight solids solution is carried out at a moderately elevated temperature 60°–80° C., preferably 65°–70° C. with toluene, and at a moderate vacuum (100–200 mm Hg) to facilitate distillation of the excess solvent.

In step (d) of the instant process slow cooling with continued agitation is required over an extended period of time in order to prevent premature precipitation of the product. Precipitous precipitation of the instant diamine by rapid cooling to low temperature increases the risk of coprecipitating residual impurities still in the toluene or xylene solution. At least an 8 hour hold at room temperature is needed to prevent such a coprecipitation of any residual impurities to occur.

Upon cooling then to 0° to 5° C., the desired product starts to crystallize. The crystallization step (e) is then greatly facilitated by the addition of a lower alkane of 5 to 8 carbon atoms or a mixture of such alkanes in a weight approximately equal to that of the toluene or xylene present. The preferred alkane is n-heptane.

The desired product is then isolated by conventional procedures and is eminently suitable for preparing polyimides or use as an epoxy curing agent, stabilizer and the like.

Any type of equipment which can provide agitation, reduced pressure capability and good temperature control can be used for carrying out the current process.

The following examples are presented for the purpose of illustration only and are not to be construed to limit the nature or scope of the invention in any manner whatsoever.

EXAMPLE 1

640 kg of a solution consisting of 16% by weight of 5(6)-amino-1-(4-aminophenyl)-1,3,3-trimethylindane and 84% by weight of toluene and an adventitious amount of water is transferred to the reactor from the reduction vessel. The temperature is adjusted to 20°–25° C. and moderate agitation is established. 71.5 kg of a 10% by weight solution of acetic acid is charged to the DAPI/toluene solution and mixed for 30 minutes. Agitation is stopped and the lower water-acetic acid phase is split off.

Maintaining the temperature at 20°–25° C., 60 kg of a slurry consisting of 83% Filtrol Grade 4 and 17% by weight of toluene is charged to the DAPI/toluene solution. After agitating the reaction mixture for 15 minutes, the acidic clay is removed by filtration.

The DAPI/toluene solution is then rinsed repeatedly with 160 kg deionized water until the solution conductivity stabilizes. The lower water phase of each rinse is split off.

After the conductivity stabilizes, vacuum is slowly applied to a pressure of 100–200 mm of Hg. The solution is then heated to a temperature between 65° and 70° C. and toluene is distilled until a DAPI content of 50% by weight is achieved.

The solution is then cooled slowly over two hours to a temperature of 23°–25° C., and held at this temperature for eight hours. The viscous solution is then slowly cooled, with mild agitation, to a temperature between 0° and 5° C. at a rate of 3° C. per hour. After eight hours, 100 kg of n-heptane is slowly charged to the crystallization mass with temperature and agitation maintained. The mass is held for one hour at 0°–5° C.

The desired product is obtained in approximately 95% yield and the crystals are stable during conventional centrifugation and have a melting range of 80°–128° C.

EXAMPLE 2

When an equal weight of dry 5(6)-amino-1-(4-aminophenyl)-1,3,3-trimethylindane (DAPI) was substituted for the dissolved material in Example 1, and the corresponding weight of toluene in Example 1 was used, pure crystalline DAPI was again produced using the general procedure of Example 1.

What is claimed is:

1. A process for preparing 5(6)-amino-1-(4-aminophenyl)-1,3,3-trimethylindane in a purified, crystalline form which comprises
   (a) mixing a solution of toluene or xylene and 5(6)-amino-1-(4-aminophenyl)-1,3,3-trimethylindane with an aqueous solution of a lower alkane monocarboxylic acid at room temperature, to extract polyamino impurities,
   (b) treating the toluene or xylene layer from step (a) with an acidic clay at room temperature to complete the removal of polyamino impurities by absorption thereon,
   (c) concentrating the toluene or xylene layer from step (b) to about a 50% by weight solution of 5(6)-amino-1-(4-aminophenyl)-1,3,3-trimethylindane by heating to a temperature between 60° and 80° C. under a pressure of 100 to 200 mm Hg to remove excess toluene or xylene,
   (d) slowly cooling the solution from step (c) with continual agitation first to room temperature, then, following an extended hold of 8 to 15 hours at room temperature, with continued slow cooling to a temperature between 0° and 5° C. to initiate crystallization of the product, and finally,
   (e) charging at 0° to 5° C. to the crystallizing mass from step (d) an alkane of 5 to 8 carbon atoms or a mixture of such alkanes in a weight equal to that of the toluene or xylene present to facilitate crystallization of the desired product which is then isolated.

2. A process according to claim 1 which comprises
   (a) mixing a solution of toluene and 5(6)-amino-1-(4-aminophenyl)-1,3,3-trimethylindane with an aqueous acetic acid solution at room temperature to extract polyamino impurities,
   (b) treating the toluene layer from step (a) with an acidic clay Filtrol grade 1, 4 or 13 to complete removal of polyamino impurities,
   (c) concentrating the toluene layer from step (b) to about a 50% by weight solution of 5(6)-amino-1-(4-aminophenyl)-1,3,3-trimethylindane by heating between 65° and 70° C. under a pressure of 100 to 200 mm Hg to remove excess toluene,
   (d) slowly cooling the solution from step (c) with continual agitation, first to room temperature, then, following an extended hold of 8 to 15 hours at room temperature, with continued slow cooling to a temperature between 0° and 5° C. to initiate crystallization of the product, and finally
   (e) charging at 0° to 5° C. to the crystallizing mass from step (d) n-heptane in a weight equal to that of the toluene present to facilitate crystallization of the desired product which is then isolated.

3. A process according to claim 2 wherein
   (a) a 10% aqueous solution of acetic acid is used, and
   (b) acidic clay Filtrol grade 4 is used.

* * * * *